(12) United States Patent
Wu et al.

(10) Patent No.: US 9,788,811 B2
(45) Date of Patent: Oct. 17, 2017

(54) IMAGING SYSTEM OF MICROBUBBLE THERAPY AND IMAGE EVALUATION METHOD USING THE SAME

(71) Applicant: National Tsing Hua University, Hsinchu (TW)

(72) Inventors: Chen-Hua Wu, Hsinchu (TW); Hsu-Hsia Peng, Hsinchu (TW)

(73) Assignee: NATIONAL TSING HUA UNIVERSITY, Hsinchu (TW)

(*) Notice: Subject to any disclaimer, the term of this patent is extended or adjusted under 35 U.S.C. 154(b) by 645 days.

(21) Appl. No.: 14/302,770

(22) Filed: Jun. 12, 2014

(65) Prior Publication Data
US 2015/0360020 A1    Dec. 17, 2015

(51) Int. Cl.
G01V 3/00      (2006.01)
A61B 8/06      (2006.01)
(Continued)

(52) U.S. Cl.
CPC .............. A61B 8/06 (2013.01); A61B 5/055 (2013.01); A61B 8/481 (2013.01); A61N 7/00 (2013.01);
(Continued)

(58) Field of Classification Search
CPC .............. G01R 33/3415; G01R 33/543; G01R 33/5659; G01R 33/36; A61B 5/055
(Continued)

(56) References Cited

U.S. PATENT DOCUMENTS 5,202,631 A * 4/1993 Harms ................. G01R 33/446
324/307
2007/0133852 A1* 6/2007 Collins .................... A61B 8/08
382/128
(Continued)

OTHER PUBLICATIONS

Wu et al., "Real-time Monitoring of Focused Ultrasound Inertial Cavitationon on Microbubbles by Gradient Echo MRI," *Joint Annual Meeting ISMRM-ESMRMB* 2014, Milan Italy, May 14, 2014.

*Primary Examiner* — Walter L Lindsay, Jr.
*Assistant Examiner* — Frederick Wenderoth
(74) *Attorney, Agent, or Firm* — Muncy, Geissler, Olds & Lowe, P.C.

(57) ABSTRACT

An imaging system of microbubble therapy cooperated with an ultrasound device for monitoring a cavitation on microbubbles in a vessel of an affected part is disclosed in the present invention, in which the cavitation is occurred by applying an ultrasound to disrupt the microbubbles. The system comprises an image acquiring module and a controlling module. The image acquiring module comprises at least one magnetic resonance device for acquiring a plurality of magnetic resonance images of the cavitation, and the controlling module provided for controlling an acquiring time of the magnetic resonance device and an irradiation time of the ultrasonic device through a controlling mode. An image evaluation method using the same is also disclosed herein and comprises steps as the following. First, injecting the microbubbles into the vessel of the affected part is performed. And then, a plurality of magnetic resonance images by a magnetic resonance device and in an acquiring time is acquired. The microbubbles are irradiated for an irradiation time by an ultrasound. Finally, changes of the magnetic resonance images will be monitored, in which an irradiation path of the ultrasound may be perpendicular to a
(Continued)

direction of flow in the vessel and the irradiation time is within the acquiring time.

18 Claims, 9 Drawing Sheets

(51) Int. Cl.
    *G01R 33/48*      (2006.01)
    *A61B 5/055*      (2006.01)
    *A61B 8/08*      (2006.01)
    *G01R 33/56*      (2006.01)
    *A61B 5/00*      (2006.01)
    *A61N 7/00*      (2006.01)
    *A61B 90/00*      (2016.01)

(52) U.S. Cl.
    CPC ........ G01R 33/4814 (2013.01); *A61B 5/4839* (2013.01); *A61B 8/0816* (2013.01); *A61B 8/5261* (2013.01); *A61B 2090/374* (2016.02); *A61M 2205/3317* (2013.01); *A61N 2007/0039* (2013.01); *G01R 33/5601* (2013.01)

(58) Field of Classification Search
    USPC .......................................................... 324/309
    See application file for complete search history.

(56) References Cited

U.S. PATENT DOCUMENTS

| | | | |
|---|---|---|---|
| 2008/0287799 A1* | 11/2008 | Hall .......................... | A61B 8/06 600/454 |
| 2010/0041989 A1* | 2/2010 | Sehgal ..................... | A61N 7/02 600/439 |
| 2010/0228122 A1* | 9/2010 | Keenan ................. | A61K 49/223 600/432 |
| 2013/0218005 A1* | 8/2013 | Desai ................. | A61B 19/2203 600/424 |

* cited by examiner

IMAGING SYSTEM OF MICROBUBBLE THERAPY AND IMAGE EVALUATION METHOD USING THE SAME

FIELD OF THE INVENTION

This invention relates to an imaging system of microbubble therapy, especially relates to an imaging system of microbubble therapy cooperated with an ultrasonic device and magnetic resonance imaging (MRI) device for real-time monitoring a cavitation on microbubbles in a vessel of an affected part and an image evaluation method using thereof.

BACKGROUND OF THE INVENTION

In present medical technology, delivering the drug to a lesion zone without passing the metabolism of the digestive system and the liver to maintain the concentration of the drug in the blood is a concerned research subject. However, it is difficult to deliver the drug to the lesion zone directly.

For example, the direct delivery of drugs to the central nervous system would make the resulting interactions highly target-specific and thereby dramatically improve the therapeutic effects and reduce possible side effect. However, it is difficult to delivery many potent therapeutic agents to the brain due to the presence of the blood-brain barrier (BBB), which is a specialized system of capillary endothelial cells that protects the brain from harmful substances. Although many methods have been developed to overcome BBB impermeability when delivering drugs, such as increasing their liquid solubility, or by the using vectors such as amino acids for carriers, none has been applied clinically.

Recently, focus ultrasound (FUS) can be used to transiently disrupt the BBB and thereby aid the noninvasive delivery of treatment agents to specific regions in the brain. Furthermore, gas-filled microbubbles (MBs) were originally developed as an intravascular contrast agent to enhance backscattering signals in ultrasound imaging. Therefore, the technique of transmitting FUS with usage of MBs is well-known as a strategy of increasing BBB permeability and therefore is able to improve the efficiency of drug delivery. The mechanical force caused by MBs inertial cavitation provides a non-invasive, transient, and reversible BBB disruption. However, although using the abovementioned method can improve the efficiency of the drug delivery, how to estimate treating conditions of an affected part of a patient is another issue for clinical staffs.

In the current technology for processing focused ultrasound therapy, several imaging modalities including magnetic resonance imaging (MRI), positron emission tomography (PET), and single photon emission computed tomography (SPECT) and contrast-enhanced ultrasound (CEUS) have been used to monitor drug pharmacokinetics. For example, MRI can also provide helpful imaging guidance not only to localize the targeting region, but also to observe the course of FUS transmission. However, it is necessary to take MRI before and after surgery, respectively, so that the clinical staff needs to go forward and backward between an operation room and an imaging room. Therefore, it is difficult to obtain real-time images for monitoring the operation status of the surgery easily. Except for the abovementioned disadvantage, it is also a load to vigor of the patient.

SUMMARY OF THE INVENTION

Accordingly, the present invention discloses an imaging system of microbubble therapy cooperated with an ultrasonic device for monitoring a cavitation on microbubbles in a vessel of an affected part, in which the cavitation is occurred by applying an ultrasound to disrupt the microbubbles. The system comprises an image acquiring module and a controlling module. The image acquiring module comprises at least one magnetic resonance device for acquiring a plurality of magnetic resonance images of the cavitation, and the controlling module provided for controlling an acquiring time of the magnetic resonance device and an irradiation time of the ultrasonic device through a controlling mode.

Preferably, the microbubbles comprise drugs for treating the affected part.

Preferably, the magnetic resonance images are gradient echo magnetic resonance images. More preferably, the abovementioned gradient echo magnetic resonance images are acquired by adopting a flip angle of 0-90 degrees (such as 20 degrees) to obtain an environment signal of microbubbles surrounding.

Preferably, the imaging system further comprising a computing module for providing a relation diagram between time and an acquiring signal intensity, in which the acquiring signal intensity is a contrast value of the magnetic resonance images acquired, respectively, at a specific time (ultrasonic irradiation) and at an initial time (no ultrasonic irradiation). More preferably, the acquiring signal intensity is a mean contrast value of several positions of the magnetic resonance images acquired, respectively, at the specific time and at the initial time of several positions.

Preferably, the controlling mode comprises a consecutive mode, an intermittent mode and a burst mode.

Preferably, the consecutive mode is performed to apply continuous ultrasound pulses for the irradiation time within the acquiring time.

Preferably, the intermittent mode is performed to apply several times of continuous ultrasound pulses spaced at intervals for the irradiation time within the acquiring time.

Preferably, the burst mode is performed to apply ultrasound pulses for the irradiation time with a duty cycle within the acquiring time.

Another object of the present invention is to provide an image evaluation method of microbubble therapy for monitoring a cavitation on microbubbles in a vessel of an affected part. The method comprises the following steps: First, injecting the microbubbles into the vessel which will flow to the affected part is performed. And then, a plurality of magnetic resonance images by a magnetic resonance device and in an acquiring time is acquired. The microbubbles are irradiated for an irradiation time by an ultrasound. Finally, changes of the magnetic resonance images will be monitored, in which an irradiation path of the ultrasound may be perpendicular to a direction of flow in the vessel and the irradiation time is within the acquiring time.

Preferably, the microbubbles comprise drugs for treating the affected part.

Preferably, the step of monitoring the changes of the magnetic resonance images further comprises a step of providing a relation diagram between time and an acquiring signal intensity in which the acquiring signal intensity is a contrast value of the magnetic resonance images acquired, respectively, at a specific time (ultrasonic irradiation) and at an initial time (no ultrasonic irradiation). More preferably, the acquiring signal intensity is a mean contrast value of several positions of the magnetic resonance images acquired, respectively, at the specific time and at the initial time of several positions.

Preferably, the magnetic resonance images are gradient echo magnetic resonance images. More preferably, the gradient echo magnetic resonance images are acquired by adopting a flip angle of 0-90 degrees (such as 20 degrees) to obtain an environment signal of microbubbles surrounding.

Preferably, the irradiation time is time for consecutively applying the ultrasound pulses.

Preferably, the irradiation time is time for applying several times of continuous ultrasound pulses spaced at intervals.

Preferably, the irradiation time is time for applying ultrasound pulses with a duty cycle.

The features and advantages of the present invention will be understood and illustrated in the following specification and FIGS. 1~7D.

BRIEF DESCRIPTION OF THE DRAWINGS

(FIG. 7A) Consecutive FUS of 8 W with 0.1×, 0.01× and 0.001× microbubbles, (FIG. 7B) 0.1× microbubbles with consecutive FUS of variant power (8, 5, 2 W), (FIG. 7C) images acquired with variant slice thickness of 3, 6, 8 mm.

DETAILED DESCRIPTION OF THE INVENTION

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention. To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Figure 1:
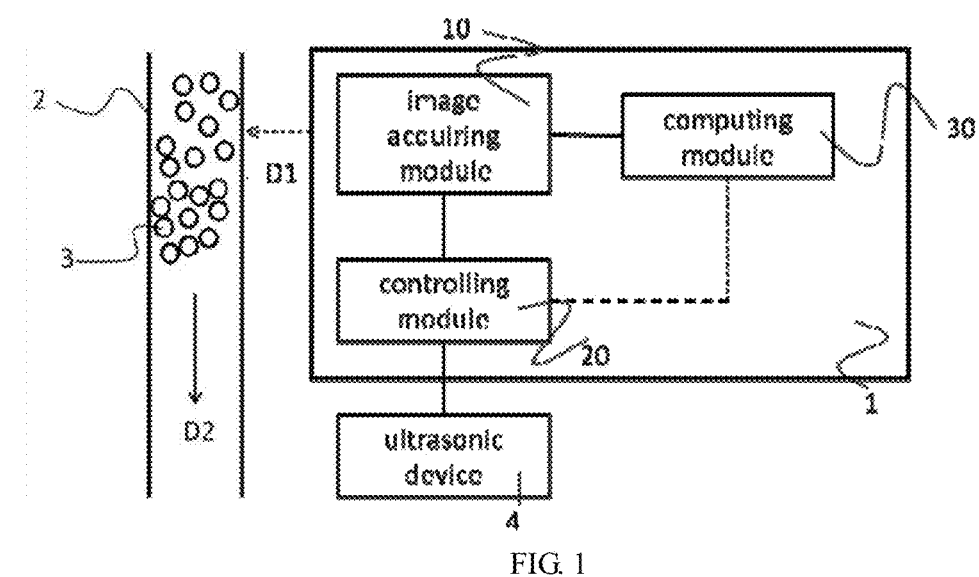
FIG. 1 is a structural schematic diagram showing an imaging system according to the present invention.
Figure 2A:
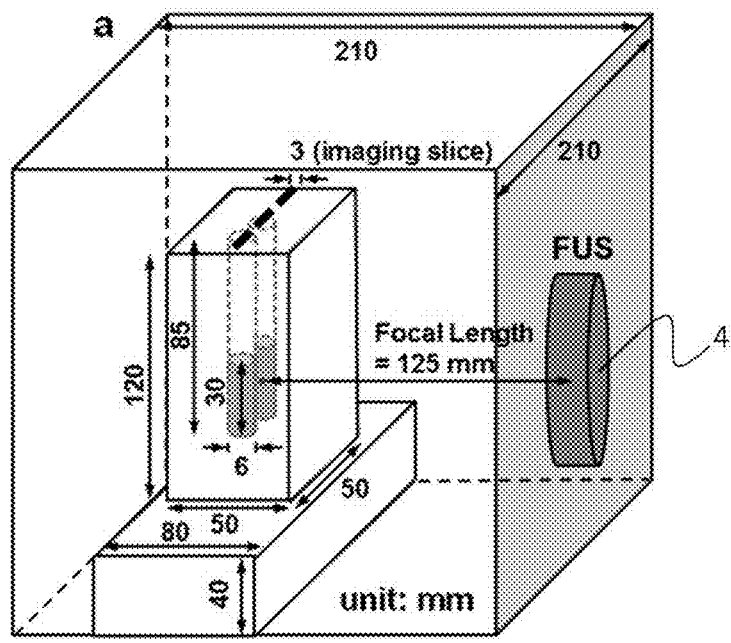
FIGS. 2A and 2B are diagram showing an experimental setup of a preferred embodiment according to the present invention.
Figure 2B:
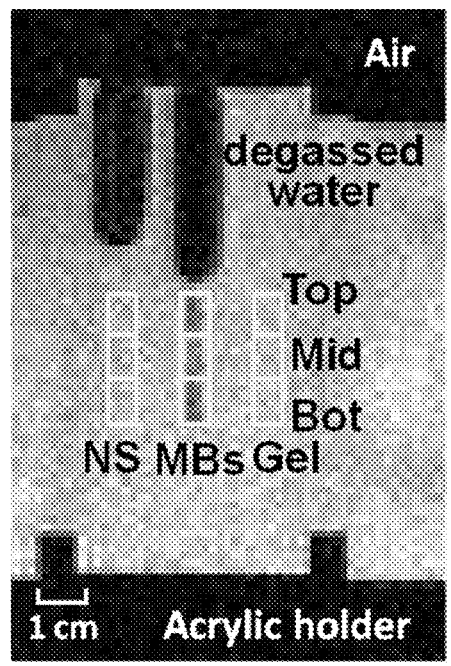

Please refer to FIG. 1 in conjunction with FIG. 2A and FIG. 2B. FIG. 1 is a structural schematic diagram showing an imaging system according to the present invention, and FIGS. 2A and 2B are diagram showing an experimental setup of a preferred embodiment according to the present invention. As shown in the figures, the present invention provides an imaging system 1 of microbubble therapy cooperated with an ultrasonic device 4 for monitoring a cavitation on microbubbles (MBs) 3 in a vessel 2 of an affected part (not shown in the figure). It is well known that the cavitation usually occurs when a liquid is subjected to rapid changes of pressure that cause the formation of cavities. In a preferred embodiment of the present invention, the cavitation is occurred by applying an ultrasound to disrupt the MBs. That is, the imaging system of the present invention is performed by cooperating with an ultrasonic device 4 (please refer to FIG. 2A). Preferably, the ultrasound is a focused ultrasound (FUS). And further, in a preferred embodiment of the present invention as shown in FIG. 2A and FIG. 2B, a single-element focused piezoelectric transducer (central frequency 1.85 MHz, 10 cm diameter, 12.5 cm curvature, Imasonic, Besancon, France) can be used as the source of FUS sonication. FUS pulses with powers of 8, 5, 2 W (watt) (8 W of acoustic pressure is measured as 2650 kPa) are applied, respectively, according to the experimental design described later. However, it is an exemplary embodiment and the present invention is not limited thereto.

Furthermore, the MBs are preferably used as drug carrier so that they comprise drugs for treating the affected part. In a preferred embodiment, the MBs are composed of liquid and $C_3F_8$, the mean diameter of the MBs can be 1.25 μm, and the concentration of that can be $(4.36±0.32)×10^{10}$ droplets/mL. However, the present invention is not limited thereto.

In the present invention, the system 1 comprises an image acquiring module 10 and a controlling module 20. The image acquiring module 10 (The following content is to use a MRI device for testing) comprises at least one magnetic resonance device for acquiring a plurality of magnetic resonance images of the cavitation, and the controlling module 20 provided for controlling an acquiring time of the magnetic resonance device and an irradiation time of the ultrasonic device 4 through a controlling mode. In an embodiment, when takes the magnetic resonance images, the controlling module is synchronous to focus the incident of the image acquiring module 10 and the ultrasonic device 4.

Moreover, the imaging system further comprises a computing module 30 for providing a relation diagram between time and acquiring signal intensity. The acquiring signal intensity is a contrast value of the magnetic resonance images acquired, respectively, at a specific time and at an initial time. More preferably, the acquiring signal intensity is a mean contrast value of several positions of the magnetic resonance images acquired, respectively, at the specific time and at the initial time of several positions. It is noted that the releasing status of the drugs released from the MBs can be monitored by monitoring the changes shown in the relation diagram. The details will be described later, and there is no need for further description herein. In an embodiment, the computing module 30 provides a revising value that feed back to the controlling module 20 for adjusting the magnetic resonance images taking more accurately.

Preferably, the abovementioned magnetic resonance images are gradient echo magnetic resonance images. In the preferred embodiment, the gradient echo sequence (TR/TE=8/3.61 ms, pixel size=1.56×1.56 mm², flip angle=20°) is performed for real-time monitoring of MBs cavitation in a 3.0 Tesla MR scanner (Trio, Siemens, Erlangen, Germany). The details will be described later, and there is no need for further description herein.

Except the imaging system described as above, the present invention further provides an image evaluation method of microbubble therapy for monitoring a cavitation on MBs in a vessel of an affected part. The method comprises the following steps: First, injecting the MBs into a vessel of an affected part is performed as shown in step S102. And then, as shown in step S104, a plurality of magnetic resonance images by a magnetic resonance device and in an acquiring time is acquired. Changes of the magnetic resonance images will be monitored in step S106. Finally, the MBs are irradiated for an irradiation time by an ultrasound in step S108.

Although it is not shown in the figure, the abovementioned step of monitoring the changes of the magnetic resonance images further comprises a step of providing a relation diagram between time and an acquiring signal intensity in which the acquiring signal intensity is a contrast value of the magnetic resonance images acquired, respectively, at a specific time and at an initial time. More preferably, the acquiring signal intensity is a mean contrast value of several positions of the magnetic resonance images acquired, respectively, at the specific time and at the initial time of several positions.

Preferably, an irradiation path of the ultrasound may be perpendicular to a direction of flow in the vessel (please refer back to FIG. 2A). And further, the irradiation time is within the acquiring time, that is, the irradiation time is less than the acquiring time.

Figure 3:
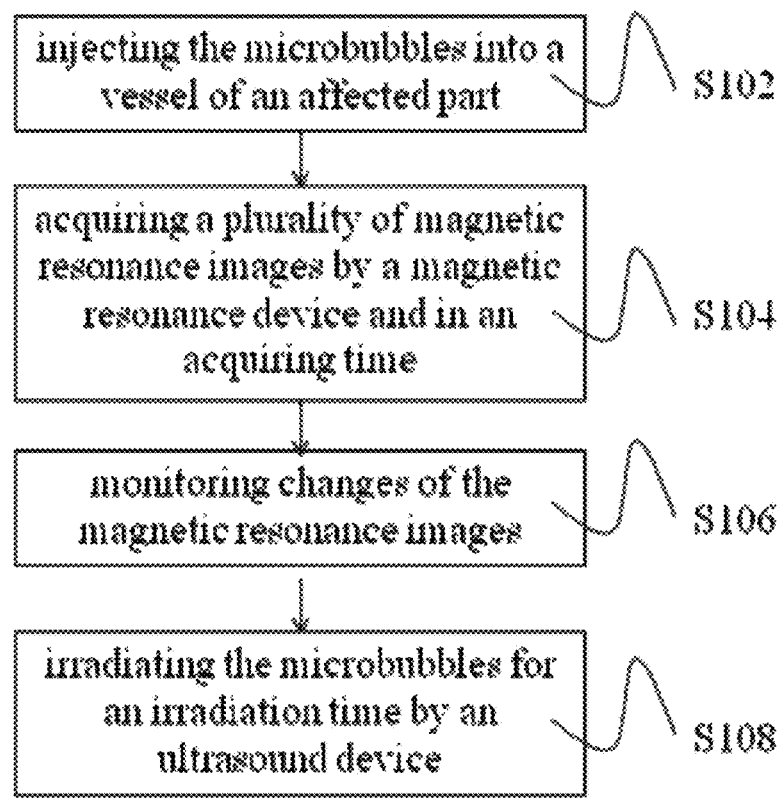
FIG. 3 is a flow chart of an image evaluation method according to the present invention.

In the following description, various experimental designs will be provided according to the abovementioned imaging system (as shown in FIG. 1, FIG. 2A and FIG. 2B) and the image evaluation method of the present invention (as shown in FIG. 3). Therefore, the concept and effect of the present invention will be further clarified. First, as mentioned before, a single-element focused piezoelectric transducer (central frequency 1.85 MHz, 10 cm diameter, 12.5 cm curvature, Imasonic, Besancon, France) can be used as the source of FUS sonication, and FUS pulses with powers of 8, 5, 2 W (8 W of acoustic pressure is measured as 2650 kPa) are applied, respectively, according to each of the experimental designs. And then, the solutions of normal saline (NS) and MBs (lipid shell with $C_3F_8$, mean diameters as Number % was 1.25 µm (range: 0.7~18 nm), concentration= $(4.36\pm0.32)\times10^{10}$ droplets/mL) are injected into a gel phantom (2% agarose) with two hollow chambers (diameter=6 mm). MBs were diluted to the concentrations of 0.1× (90% NS+10% MBs), 0.01×, and 0.001×.

Furthermore, the gradient echo sequence (TR/TE=8/3.61 ms, pixel size=1.56×1.56 mm², flip angle=20°) was performed for real-time monitoring of MBs cavitation in a 3.0 Tesla MR scanner (Trio, Siemens, Erlangen, Germany). To clarify the effect of signal drops and mimic the condition for in vivo experiments where slice thickness may be larger than vessels, experiments were acquired with slice thicknesses of 3, 6, 8 mm. All images were acquired at the focal plane and were perpendicular to the direction of ultrasound beams. Temporal resolution was 0.8 s and 270 measurements (216 s) were acquired.

Preferably, the abovementioned controlling mode can be one of the following three modes: consecutive mode, an intermittent mode and a burst mode. In practically, the present invention can adopt one of the above three designs of FUS to disrupt MBs.

Figure 4A:
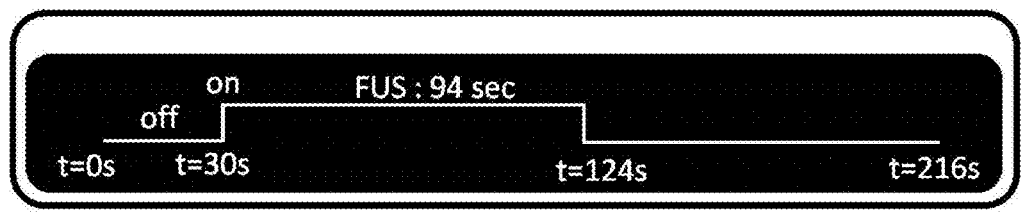
FIGS. 4A to 4C are diagrams showing experimental designs of three FUS modes according to the present invention.
Figure 4B:
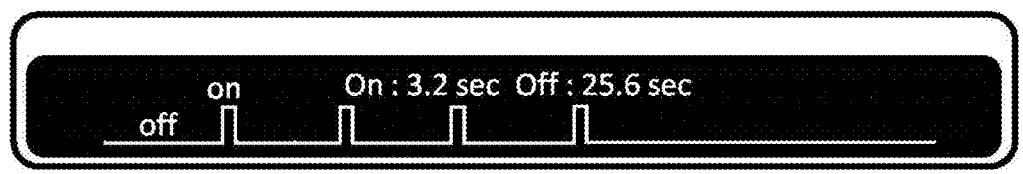
Figure 4C:
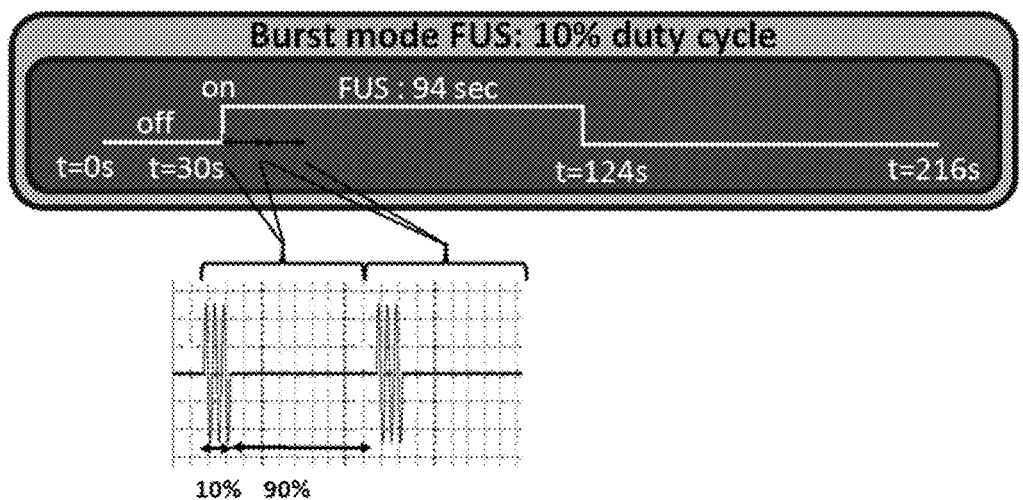

In the consecutive FUS mode, it is performed to apply continuous FUS pulses for the irradiation time, such as consecutive 94 s (ON: t=30 s, OFF: t=124 s), within the acquiring time, such as 216 s, as shown in FIG. 4A. In the intermittent mode, it is performed to repeated such as 4 times of continuous FUS pulses in a manner of interleaved ON-OFF (ON: 3.2 s, OFF: 25.6 s) as shown in FIG. 4B. In the burst mode, it is performed to apply FUS pulses for consecutive 94 s (ON: t=30 s, OFF: t=124 s) with 10% duty cycle, 18500 cycles, and burst period: 0.1 s as FIG. 4C so that to approach the conditions of in vivo experiments. It is clearly that the ultrasonic device is preferably switched on after the perturbation of the magnetic resonance imaging is stabilized.

To evaluate changes of signal intensity (SI), regions of interesting (ROIs) are selected manually at top, mid (at focal point), and bottom (Bot) parts in chambers of MBs, NS, and gel (as shown in FIG. 2B). The $SI_{MB}$ within ROI was normalized to SI of mean SI before turning-on of FUS pulses (pre-FUS): normalized $SI=(SI_{MB}/SI_{PRE-FUS_{MB}})\times100\%$.

Figure 5:
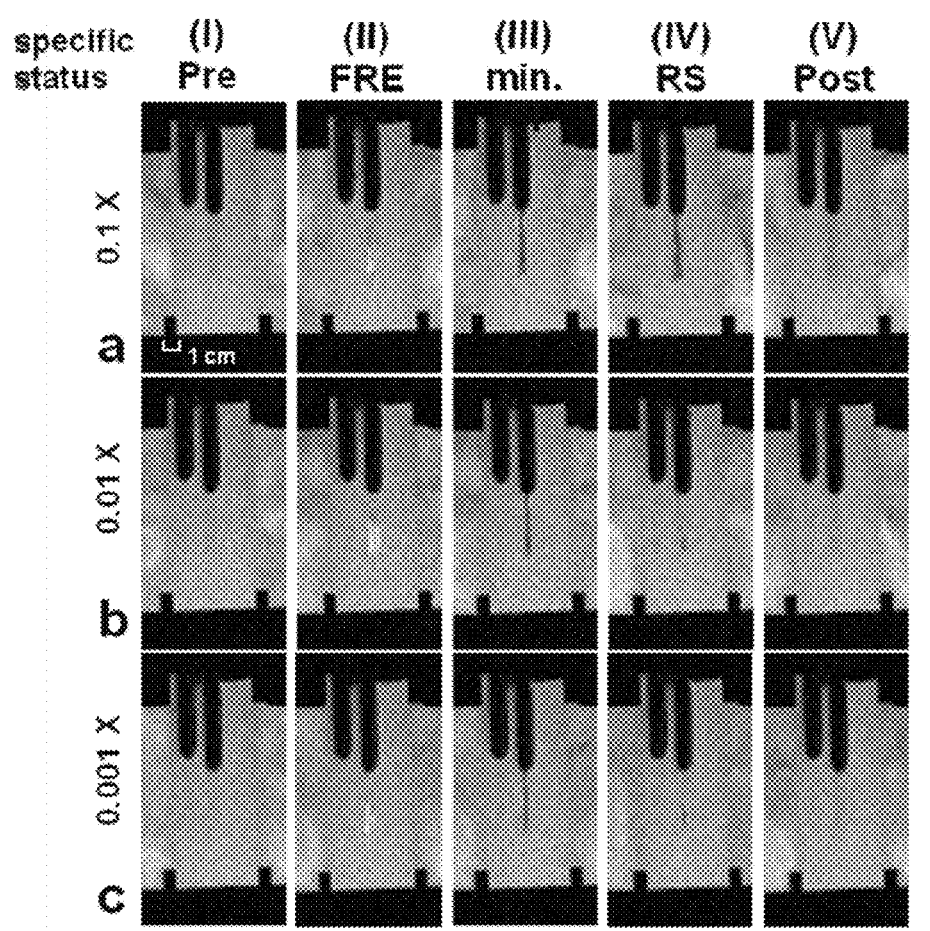
FIG. 5 are magnitude images acquired with 0.1× (a), 0.01× (b), and 0.001× (c) microbubbles at status I-V of the experimental process.

Please refer to FIG. 5, which comprises magnitude images acquired with 0.1× (a), 0.01× (b), and 0.001× (c) MBs at status I-V of the experimental process. Status (I) represents Pre-FUS, status (II) represents flow-related enhancement (FRE) at the beginning of FUS transmission, status (III) represents minimal SI, status (IV) represents signal in a recover state (RS), and status (V) represents Post-FUS.

Figure 6A:
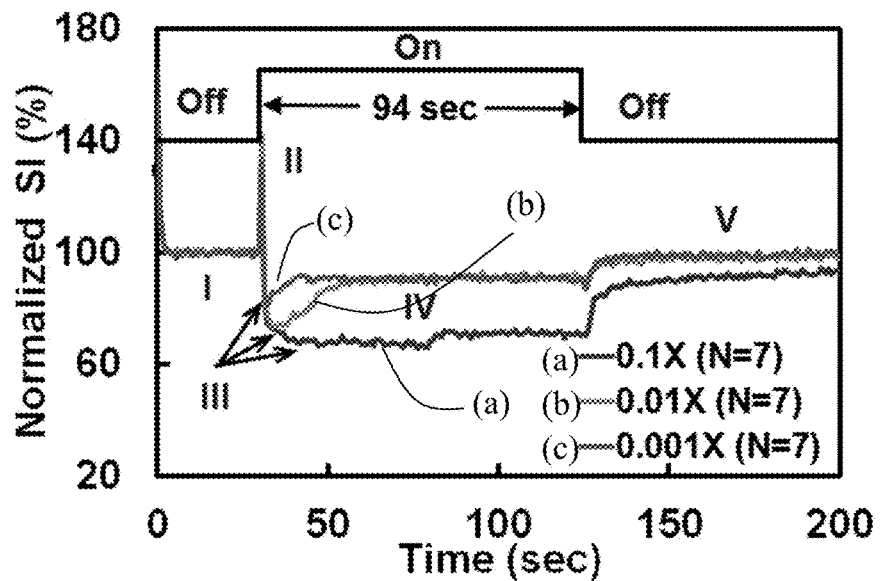
FIGS. 6A to 6C are diagrams showing the time courses of normalized signal intensity of experiments with 0.1×, 0.01× and 0.001× microbubbles for consecutive FUS (in 8 W) (FIG. 6A), intermittent FUS (in 8 W) (FIG. 6B), burst FUS (in 2 W) (FIG. 6C) mode.
Figure 6B:
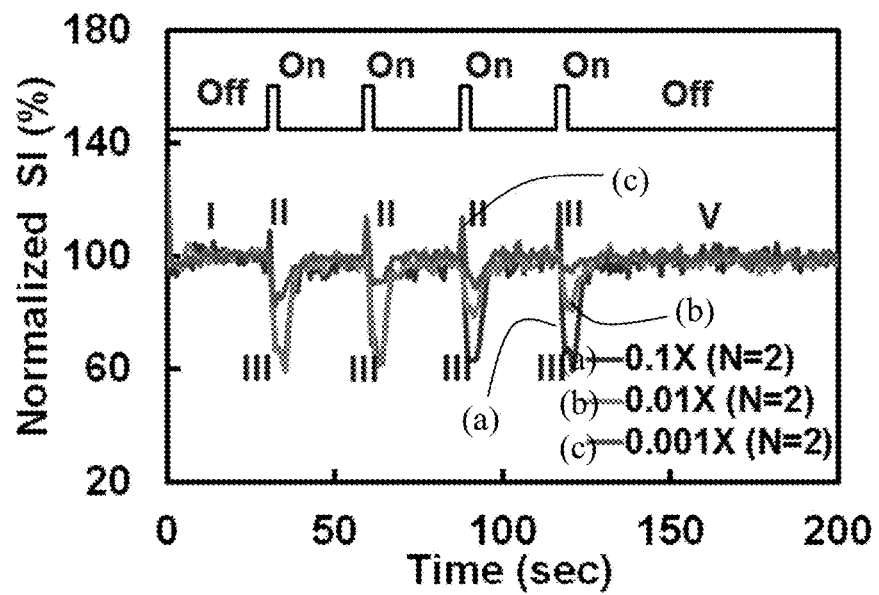
Figure 6C:
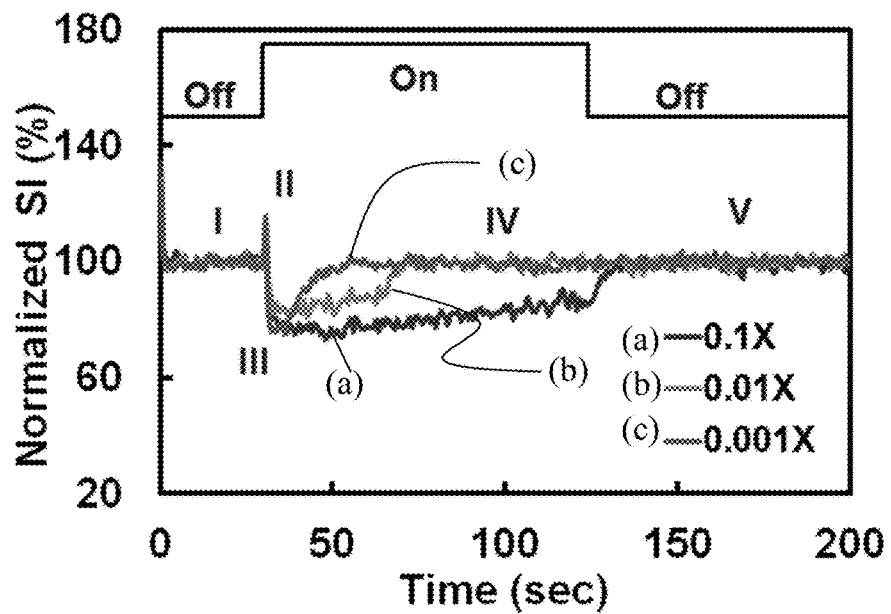
Figure 6D:
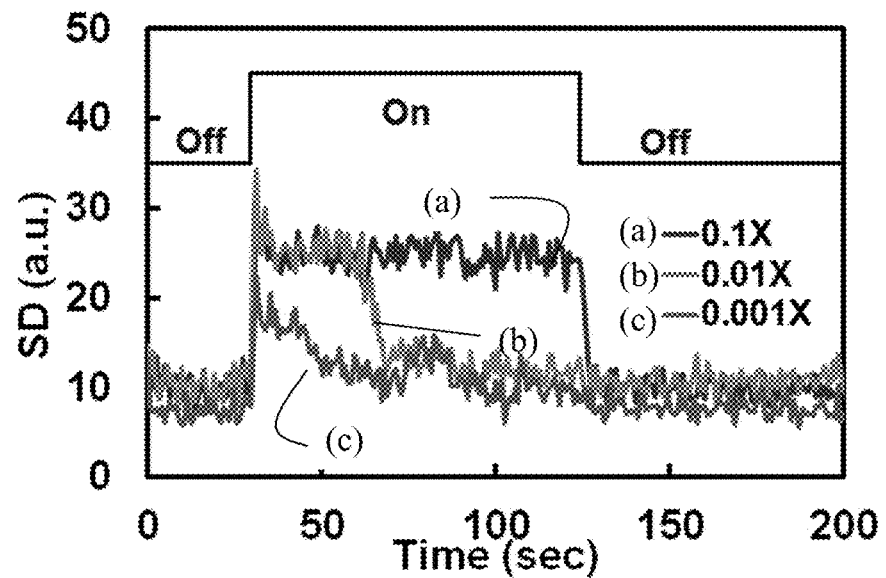
FIG. 6D is the standard deviation (SD) changes of burst mode experiments with 0.1×, 0.01×, and 0.001× of microbubbles (in 2 W)

Each status will be further indicated in FIG. 6A to FIG. 6D as well. FIGS. 6A to 6C are diagrams showing the time courses of normalized signal intensity of experiments with 0.1× (a), 0.01× (b) and 0.001× (c) MBs for consecutive FUS (FIG. 6A), intermittent FUS (FIG. 6B), burst FUS (FIG. 6C) mode, respectively. At either mode, the effect of FRE, owing to the replenishment of fresh protons inflowing into imaging slice at status (II), can be observed clearly at the beginning of each FUS transmission. The normalized SI drops from 100% to a minimum of 60~75% at status (III). In consecutive mode, with higher concentrations of MBs exhibits longer periods of reduced SI (status of (III) and (IV)): 94.4, 15.6, 4.4 sec for 0.1×, 0.01× and 0.001× of MBs, respectively (FIG. 6A). In intermittent mode with 4 times of interleaved On-Off FUS transmission, 0.1× MBs demonstrates significant decreased SI (~60%), as shown in FIG. 6B. In contrast, 0.01× shows SI of 60% in the first two times of FUS transmission and less reduced SI of 80% in the last two. MBs with 0.001× shows much minor reduced SI, particularly in the last three times of transmission. In FIG. 6C, burst mode exhibits a longer period of reduced SI compared to consecutive mode. Since temporal resolution in MRI is much lower compared with that of occurrence of FUS cavitation, a longer period of reduced SI may be beneficial for observing SI changes. Furthermore, FIG. 6D shows the standard deviation (SD) changes of burst mode experiments with 0.1×, 0.01×, and 0.001× of MBs. Significant changes of SD during transmitting FUS pulses indicated the complex vortical flow attributed to cavitation effect and locally disturbed flow around focus.

Figure 7A:
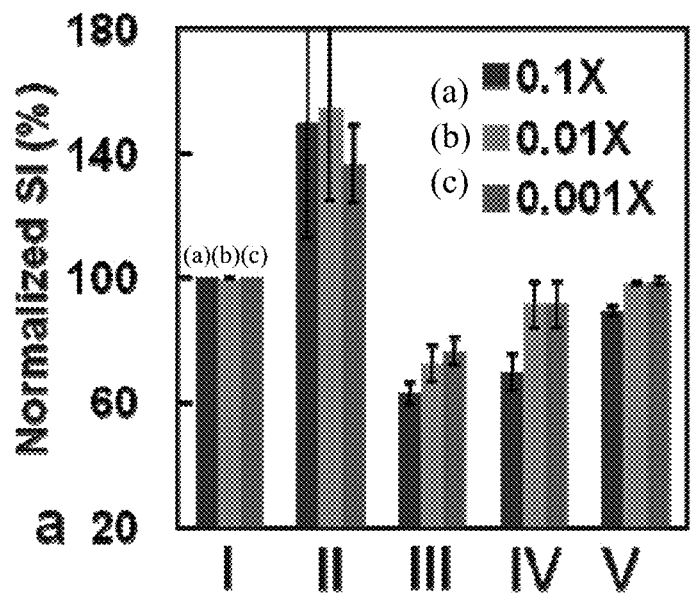
FIGS. 7A to 7C are diagrams showing the normalized signal intensity with different experimental conditions.
Figure 7B:
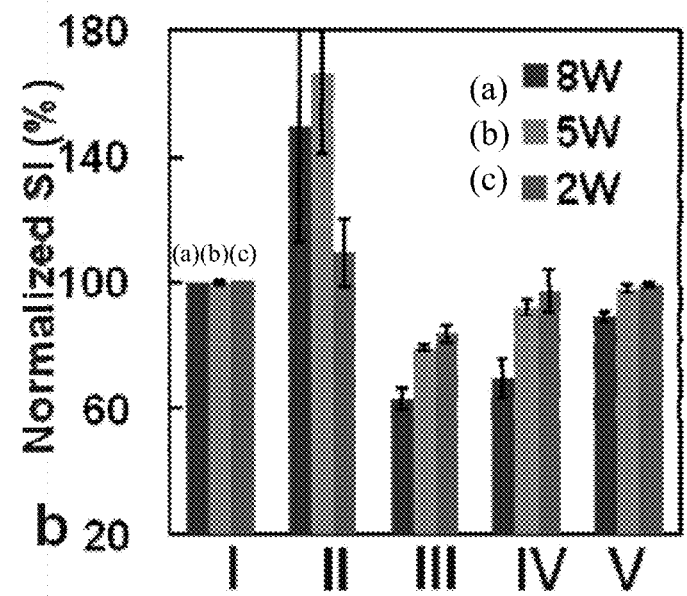
Figure 7C:
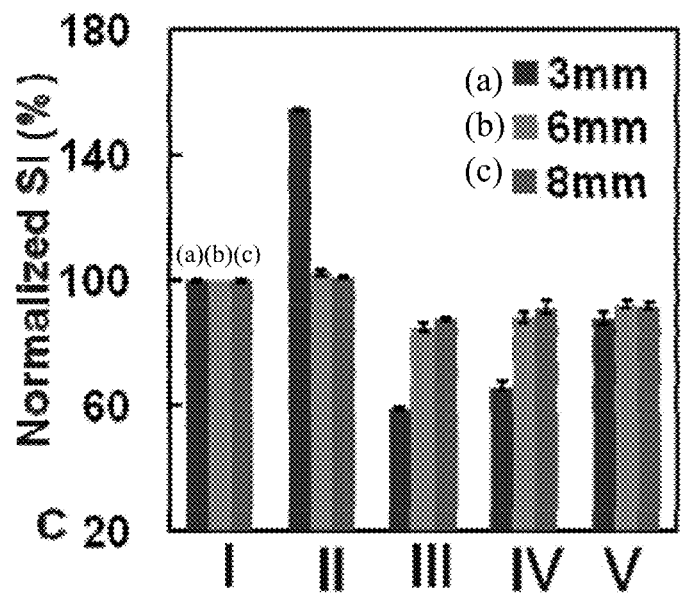
Figure 7D:
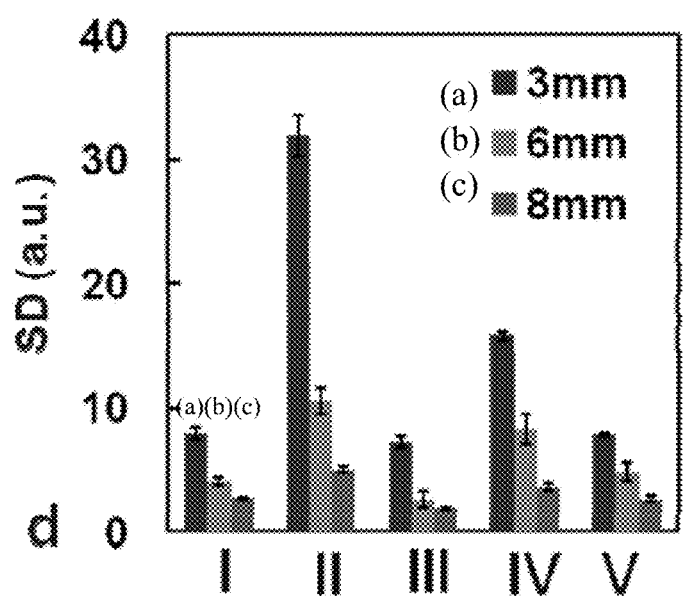
FIG. 7D is the SD of experiments for slice thickness of 3, 6, 8 mm.

Please refer to FIGS. 7A to 7C, which are diagrams showing the normalized signal intensity with different experimental conditions: (FIG. 7A) Consecutive FUS of 8 W with 0.1× (a), 0.01× (b) and 0.001× (c) MBs, (FIG. 7B) 0.1× microbubbles with consecutive FUS of variant power (8, 5, 2 W represented by bar (a), (b), (c) respectively), (FIG. 7C) images acquired with variant slice thickness of 3, 6, 8 mm represented by bar (a), (b), (c), respectively, and FIG. 7D is the SD of experiments for slice thickness of 3, 6, 8 mm represented by bar (a), (b), (c), respectively. As shown in status (II) of FIG. 7C, acquiring images with slice thickness thicker than chamber diameter, FRE effect cannot be observed. Nevertheless, the reduced SI can be observed clearly at statuses of (III) or (IV).

Under these diluted concentrations of 0.001× MBs, which was close to in vivo experiments, long-lasting reduced SI is able to be observed, demonstrating the possibility of the present invention being used for in vivo experiments. Whenever consecutive, intermittent, or burst mode of FUS pulses were applied, apparent signal drops displayed significantly (FIG. 5 and FIGS. 6A to 6D). In the present invention, SI changes under different concentrations of MBs, FUS powers, and imaging slice thicknesses are further investigated. Even with conditions of diluted MBs of 0.001×, low FUS power of 2 W, or thicker slice of 8 mm, reduced SI still can be observed (FIG. 7A to 7D). As for the FRE effect, it might attribute to the fresh spins inflowing into the imaging slice and exhibited only while imaging slice thickness is thinner than chamber diameter as shown in status (II) of FIG. 7C.

To sum up, the present invention provides an imaging system and an image evaluation method using the same for real-time monitoring the process of FUS cavitation on MBs. That is, the pulse sequence of gradient echo has been proved to be a useful technique for real-time monitoring of SI changes when transmitting FUS to MBs so that the present invention can effectively improve disadvantages as mentioned above.

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims.

We claim:

1. An imaging system of microbubble therapy coordinated with an ultrasonic device for monitoring a cavitation on microbubbles in a vessel of an affected part, wherein the cavitation is created by applying an ultrasound to disrupt the microbubbles, comprising:
   an image acquiring module comprising at least one magnetic resonance device for acquiring a plurality of magnetic resonance images of the cavitation; and
   a controlling module provided for controlling an acquiring time of the magnetic resonance device and an irradiation time of the ultrasonic device through a controlling mode, wherein the controlling mode comprises a consecutive mode, an intermittent mode and a burst mode; and
   a computing module for providing a relation diagram between time and an acquiring signal intensity, wherein the acquiring signal intensity is a contrast value of the magnetic resonance images acquired, respectively, at a specific time and at an initial time.

2. The imaging system according to claim 1, wherein the microbubbles comprise drugs for treating the affected part.

3. The imaging system according to claim 1, wherein the magnetic resonance images are gradient echo magnetic resonance images.

4. The imaging system according to claim 3, wherein the gradient echo magnetic resonance images are acquired by adopting a flip angle of 0-90 degrees.

5. The imaging system according to claim 1, wherein the acquiring signal intensity is a mean contrast value of several positions of the magnetic resonance images acquired, respectively, at the specific time and at the initial time of several positions.

6. The imaging system according to claim 1, the computing module provides a revising value that is fed back to the controlling module for adjusting the magnetic resonance images taken.

7. The imaging system according to claim 1, wherein the consecutive mode is performed to apply continuous ultrasound pulses for the irradiation time within the acquiring time.

8. The imaging system according to claim 1, wherein the intermittent mode is performed to apply several times of continuous ultrasound pulses spaced at intervals for the irradiation time within the acquiring time.

9. The imaging system according to claim 1, wherein the burst mode is performed to apply ultrasound pulses for the irradiation time with a duty cycle within the acquiring time.

10. An image evaluation method of microbubble therapy for monitoring a cavitation of microbubbles in a vessel of an affected part, comprising steps:
    injecting the microbubbles into the vessel of the affected part;
    acquiring a plurality of magnetic resonance images by a magnetic resonance device and in a acquiring time;
    irradiating the microbubbles for an irradiation time by an ultrasound, wherein the irradiation time is within the acquiring time; and
    monitoring changes of the magnetic resonance images, and providing a relation diagram between time and an acquiring signal intensity, wherein the acquiring signal intensity is a contrast value of the magnetic resonance images acquired, respectively, at a specific time and at an initial time.

11. The image evaluation method according to claim 10, wherein an irradiation path of the ultrasound is perpendicular to the direction of flow in the vessel.

12. The image evaluation method according to claim 10, wherein the microbubbles comprise drugs for treating the affected part.

13. The image evaluation method according to claim 10, wherein the acquiring signal intensity is a mean contrast value of several positions of the magnetic resonance images acquired, respectively, at the specific time and at the initial time of several positions.

14. The image evaluation method according to claim 10, wherein the magnetic resonance images are a plurality of gradient echo magnetic resonance images.

15. The image evaluation method according to claim 14, wherein the gradient echo magnetic resonance images are acquired by adopting a flip angle of 0-90 degrees.

16. The image evaluation method according to claim 10, wherein the irradiation time is time for consecutively applying the continuous ultrasound pulses.

17. The image evaluation method according to claim 10, wherein the irradiation time is time for applying several times of continuous ultrasound pulses spaced at intervals.

18. The image evaluation method according to claim 10, wherein the irradiation time is time for applying ultrasound pulses with a duty cycle.

* * * * *